United States Patent [19]

Lange et al.

[11] Patent Number: 4,605,629
[45] Date of Patent: Aug. 12, 1986

[54] METHOD OF ELUTING REAGENT FROM REAGENT STRIPS FOR CHEMICAL ANALYSES AND REAGENT STRIP THEREFOR

[75] Inventors: Hans Lange, Lampertheim; Edda Geisler; Wolfgang Werner, both of Mannheim, all of Fed. Rep. of Germany

[73] Assignee: Boehringer Mannheim GmbH, Mannheim, Fed. Rep. of Germany

[21] Appl. No.: 634,667

[22] Filed: Jul. 27, 1984

Related U.S. Application Data

[63] Continuation of Ser. No. 328,313, Dec. 7, 1981, abandoned.

[30] Foreign Application Priority Data

Dec. 23, 1980 [DE] Fed. Rep. of Germany ....... 3048799

[51] Int. Cl.$^4$ .................... G01N 21/78; G01N 33/52
[52] U.S. Cl. ....................... 436/166; 422/56; 422/58; 435/805; 436/169
[58] Field of Search .................... 422/55–58; 436/166, 169, 170; 435/805

[56] References Cited

U.S. PATENT DOCUMENTS

| 3,802,842 | 4/1974 | Lange et al. ............. 422/57 X |
| 3,912,655 | 10/1975 | Shukla et al. ............. 422/56 X |
| 4,061,468 | 12/1977 | Lange et al. ............. 422/56 |
| 4,193,766 | 3/1980 | Daunora et al. ............. 422/56 X |
| 4,219,334 | 8/1980 | Shluter et al. ............. 422/56 X |
| 4,233,089 | 9/1980 | Rothe et al. ............. 422/56 X |
| 4,234,316 | 11/1980 | Hevey ............. 422/57 X |

FOREIGN PATENT DOCUMENTS 1349623 4/1974 United Kingdom .

*Primary Examiner*—Arnold Turk
*Attorney, Agent, or Firm*—Felfe & Lynch

[57] ABSTRACT

The present invention provides a method of improving reagent elution from a reagent strip comprising a handle on one end which is affixed an absorbent carrier impregnated with a reagent. The absorbent carrier is pressed against the handle by a thin mesh which is stuck or sealed on to the handle on opposite sides of the carrier. Another mesh is between the carrier and the handle. When the carrier is immersed in a liquid, the meshes improve the elution of the reagent into the liquid.

14 Claims, 4 Drawing Figures

METHOD OF ELUTING REAGENT FROM REAGENT STRIPS FOR CHEMICAL ANALYSES AND REAGENT STRIP THEREFOR

This application is a continuation of application Ser. No. 328,313, filed Dec. 7, 1981 and abandoned herewith.

This invention relates to a new method for the chemical analysis of components of liquids. In addition, the invention relates to solid reagents a reagent strip for chemical analysis.

Since a direct physical or physicochemical analysis is only possible in special cases, chemical analysis, i.e. the addition of appropriate reagents and the determination of the reaction thereby brought about, is still the most important qualitative and quantitative method of investigating components of liquids. The reagents are frequently added in excess but, in the case of other analysis processes, such as kinetic determinations or volumetric analyses, the reagents must be added in precise amounts. In order to ensure good measurability, solid reagents are normally dissolved in an appropriate solvent and an aliquot of the solution used for the analysis. In order to save the user laborious weighings and dissolvings, especially when using several reagents, such reagent solutions have long been commercially available in a form ready for use. Reagents which are incompatible with one another in solution must be dissolved separately and mixed together shortly before use. Reagents which are unstable in solution are usually made available in the form of "reagent tablets", with the addition of appropriate tabletting adjuvants, or as lyophilisates in ampoules which can be reconstituted shortly before use by the addition of a solvent to give reagent solution. However, reagent tablets suffer from the disadvantage that in the course of production and also during storage they can change in weight, due to friction, thus resulting in a change in the amount of reagents or they must be hard pressed to such a degree that it is difficult to dissolve them. A disturbance of the analysis by the tabletting adjuvants, especially lubricants and mould release agents, also limits their general applicability.

Lyophilisation of reagent solutions in ampoules provides an optimum solution to the problem from the point of view of reconstitution and also permits mutually "incompatible" reagents to be frozen one over the other and dried in the form of "layer lyophilisates". However, this process is very laborious and expensive.

In Federal Republic of Germany Pat. No. 2,301,999, it has been suggested to stabilise substances which are unstable in solution by impregnating an absorbent carrier, for example filter paper, with the reagent solution and then drying or lyophilising it. Carrier pieces of appropriate size and thus with appropriate amounts of reagent are stuck on to handles, for example made of synthetic resin, to give "mixed rodlets". By stirring an appropriate amount of a solvent or of a test liquid with these mixed rodlets, the reagents are eluted again and the final analysis mixture is obtained. Although, in principle, this technique is useful, it has been found that very readily soluble materials are quickly and completely dissolved from the mixed rodlets but that many conventional reagents are incompletely eluted. Quite apart from the fact that unnecessarily large amounts of reagents must be impregnated into the carrier, the eluted amount is also dependent upon the conditions of elution (time, speed of stirring, temperature, viscosity and the like) so that an exact reagent concentration cannot be guaranteed.

Thus, the problem exists of improving the above-mentioned "mixed rodlets" in such a manner that reagent strips are obtained from which the reagents can be dissolved out quickly, reproducibly and as completely as possible.

Thus, according to the present invention, there is provided a handle on the lower part of which is affixed an absorbent carrier impregnated with a reagent. The absorbent carrier is pressed against the handle by a thin, carrier-covering mesh which is stuck or sealed on to the handle on opposite sides of the carrier.

Sealing reagent-containing absorbent carriers between a synthetic resin handle and a thin mesh has already been described in Federal Republic of Germany Pat. No. 2,118,455 but in the therein described test papers with dimensions of about $6 \times 6$ mm., a "leaching out" effect is not observed even in a stream of urine (see column 3, lines 76–16). Therefore, it is surprising that, by brief stirring in a solvent, the reagents are eluted practically quantitatively from such a reagent strip, whereas they are only incompletely dissolved out of a carrier according to Federal Republic of Germany Pat. No. 2,301,999 in which the upper surface is completely free for the entry of solvent.

The rate of dissolving out can be further increased when thicker papers (absorbent carriers), necessary for taking up comparatively large amounts of reagents, are divided up into several layers of thinner paper, a transverse flow thereby being brought about. Such separate layers of paper can also serve physically to separate incompatible reagents from one another.

Furthermore, the throughflow and thus the rate of elution can be improved when, between such paper layers or between the paper and the handle, there is provided a further, preferably synthetic resin mesh. When different reagents are used in different paper layers, such intermediate meshes prevent a possible interaction.

Although, in principle, natural fibre and metal wire meshes can be used, because of the simple working up and the more favourable price, it is preferred to use synthetic resin meshes made, for example, of polyamide, polyester, polyvinyl choride or the like, for the covering, intermediate and underlying meshes. Mesh sizes of 50 to $250\mu$ and preferably of 100 to $150\mu$ have proved to be useful for the covering mesh and mesh sizes of 80 to $250\mu$ and preferably of 100 to $200\mu$ for the underlying meshes. The filament thickness is usually from 10 to $50\mu$. Woven or knitted meshes can both be used in the same manner and the individual filaments can be welded or stuck together at the crossover points.

The absorbent carriers used are preferably papers or fleeces of cotton, cellulose, regenerated cellulose or synthetic resins, for example of polyamide, polyester or the like, or mixtures thereof, although, of course, materials which undergo a chemical bonding or reaction or which form solid complexes with the reagents are excluded. Because of the ease of dissolving out therefrom and good absorbency, as well as good working up even after impregnation with many reagents, it is especially preferred to use polyamide or polyamide/cellulose papers.

The reagent strips according to the present invention also permit sensitive and solid reagents to be stored in stable form and to be quickly reconstituted to give reagent solutions. By means of the thickness and size of the carrier used, as well as the concentration of the reagent solution used for the impregnation, the reagent concentration in the final solution can be controlled or regulated within wide ranges. When comparatively large amounts of reagents are required, several papers can also be affixed to a handle either on top of one another or side by side. The distribution of the reagents on to several pieces of paper permits appropriate reagent papers for different tests, for example buffer mixtures, to be produced together and, in the case of the sealing in, to be combined in an appropriate manner.

DESCRIPTION OF THE DRAWINGS

The construction of the reagent strips according to the present invention is illustrated, by way of example, in the accompanying drawings, in which.

DESCRIPTION OF THE PREFERRED EMBODIMENTS

Figure 1:
FIG. 1 is a side view of first preferred embodiment.
Figure 2:
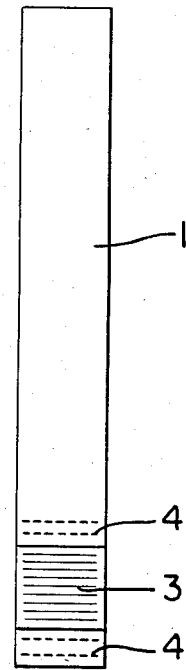
FIG. 2, is a top view of the embodiment shown in FIG. 1.

FIGS. 1 and 2 show side and top views of a reagent strip according to the present invention with a handle (1), a reagent paper (2) and a covering mesh (3), which is connected to the handle at the fixing points (1).

Figure 3:
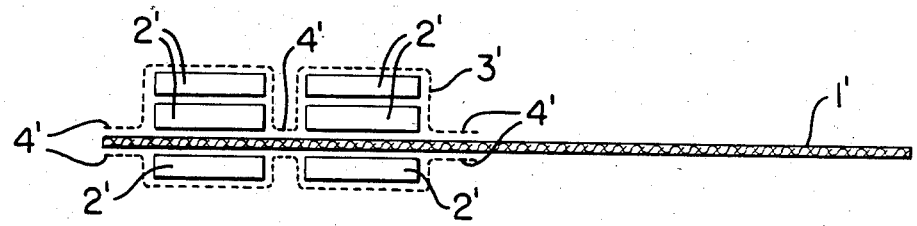
FIG. 3 is a side view of a second preferred embodiment.

FIG. 3 shows a side view of a reagent strip with two separate, double-layer reagent papers 2' on one side of the handle 1' and two separate single layer reagent papers 2' on the other side thereof.

Figure 4:
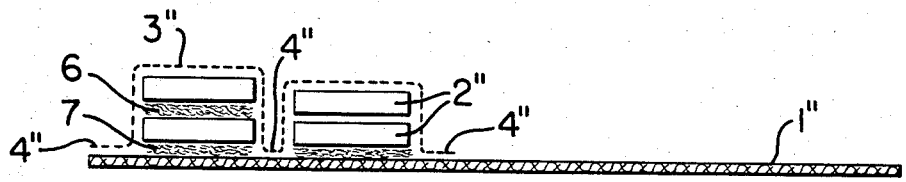
FIG. 4 is a side view of a third preferred embodiment.

FIG. 4 shows a further reagent strip in which the reagent papers are separated by an intermediate mesh (6) and are raised from the handle 1″ by an underlying mesh (7).

The test strips are preferably produced by the continuous sealing or sticking together of long strips of synthetic resin, reagent paper and mesh in a known sealing device. Cutting up the bands obtained in a transverse direction to give strips of the desired breadth can be carried out in a manner analogous to that described in Federal Republic of Germany Pat. No. 2,118,,455.

For the tests described in the following Examples, the reagent strips were correspondingly produced, although laboratory samples or small quantities can, of course, also be produced by moistening previously produced "empty" reagent strips with a measured amount of a reagent solution, followed by drying.

The following Examples are given for the purpose of illustrating the present invention:

EXAMPLE 1

Reagent strips for the determination of glutamate-oxalacetate transaminase (GOT) in serum Into a measurement cuvette of 10 mm. path-length there is introduced a reagent strip of 7-8 cm. length and 6 mm. breadth, which is stable when stored in dry form for a year at ambient temperature and on the lower end of which are affixed two zones separated from one another, each being a reagent paper with a surface area of 6×6 mm. placed between a fine-mesh fabric of about 120μ mesh size and a carrier foil. One zone contains 0.4μ mole of nicotinamide-adenine-dinucleotide (NADH), 0.2 mg. sodium carbonate and 0.3 mg. sodium bicarbonate and the other zone contains 28μ mole α-ketoglutarate, 1.7 U lactate dehydrogenase (LDH), 1.1 U malate dehydrogenase (MDH) and 0.2 mg. tris-(hydroxymethyl)-aminomethane (tris buffer).

Subsequently, there are added 2 ml. of substrate-buffer mixture of pH 7.8 which can be kept for one year at ambient temperature and which contains 88 mMole/liter tris-(hydroxymethyl)-aminomethane, 264 mMole/liter sodium L-aspartate and 0.5 g. sodium azide. 0.2 ml. Serum is then pipetted in and well mixed with the reagent strip for about 5 seconds, whereafter the strip is removed and the liquid test mixture left to stand for 2 minutes at ambient temperature.

The activities of the glutamate-oxalacetate transaminase (GOT) are then measured photometrically at 334 nm, 340 nm or 366 nm by continuous recording or by reading off the extinction at definite intervals of time (for example after every 60 seconds). If a comparatively large amount of reagent solution is to be prepared, for example 10 ml. for a series of measurements, then this can be simply accomplished by increasing the reagent carrier surface area from 0.36 cm$^2$ with the described substance concentration to, for example, 1.8 cm$^2$ (reagent strips 10 mm. wide and the sealed in reagent papers have a surface area of 18×10 mm.).

If such a strip is eluted for about 5 to 10 seconds into 10 ml. of the above-described buffer-substrate mixture, then a reaction solution is obtained with the following composition:

tris buffer (pH 7.8): 88 mMole/l.
L-aspartate: 264 mMole/l.
NADH: 0.20 mMole/l.
LDH: 660 U/l.
MDH: 460 U/l.
α-ketoglutarate: 13.2 mMole/l.

This solution can be used in the conventional way for a series of measurements.

EXAMPLE 2

Reagent strips for the determination of triglycerides in serum

In an appropriate glass vessel in which has been placed 13 ml. of a buffer solution of pH 8.1 which is stable for over a year at ambient temperature and which contains 0.1 mole/l. glycylglycine, 0.16 mole/liter ammonium chloride, 1 mMole/liter sodium cholate, 0.2% detergent and 1 g./liter sodium azide, there is placed a reagent strip of about 100 mm. length and 10 mm. breadth which, in two zones, contains two overlying reagent papers with a surface area of 10×15 mm. sealed in a manner analogous to that described in Example 1. For accelerating the dissolving of the substances, below the reagent paper zones there is additionally laid, in each case, a fabric of about 250 mesh size with a surface area of 10×15 mm. The reagent test zone affixed to the lower end of the reagent strip contains on one reagent carrier 13 mg. NAD and on the opposite lying reagent carrier 3.9 mg. 3-(4,5-dimethylthiazolyl-2)-2,5-diphenyltetrazolium bromide (MTT).

The reagent zone lying adjacent thereto contains two reagent carriers each with 45 U glycerol dehydrogenase, 6 U diaphorase and 13 U cholesterol esterase.

The reagent strips are moved intensively for 5 seconds, subsequently left to stand for 5 minutes, again moved for 5 seconds and the eluted reagent carrier discarded. A reaction solution is obtained with the following composition:

glycylglycine: 0.1 mole/l .
ammonium chloride: 0.16 mole/l.

sodium cholate: 1 mMole/l.
detergent: 2%
MTT: 270 mg./l.
NAD: 1000 mg./l.
glycerol dehydrogenase: 6 KU/l.
diaphorase: 400 U/l.
cholesterol esterase: 900 U/l.

The triglyceride content in serum is determined by adding 0.020 ml. of sample to 2 ml. of this reaction solution and, after incubating for 30 minutes at 20° to 25° C., determining the extinction at Hg 578 nm against a reagent blank (RB). The concentration (C) of the triglycerides is calculated from the following equation:

$$C[mg./100\ ml.] = 498.5 \times (E - E_{RB})$$

EXAMPLE 3

Reagent strips for the determination of uric acid in serum

Into an appropriate glass vessel containing 80 ml. of a 0.1 molar potassium phosphate buffer solution (pH 7.0), which is stable for a year at ambient temperature and which additionally contains 0.5% detergent and 1 mMole/liter of N-ethyl-N-(2-hydroxyethyl)-m-toluidine (EHT), there is placed a reagent strip of about 120 mm. length and 10 mm. width which, in each of three zones, contains two overlying reagent carriers with a surface area of 10×15 mm. held by a mesh in a manner analogous to that of the preceding Examples. The two zones affixed on the lower end of the reagent strip contain, per reagent carrier, 2.5 mg. 3-methylbenzthiazolone hydrazone-6-sulphonic acid (SMBTH) together, in each case, with 1.7 mg potassium ferrocyanide and, overlying, in each case on reagent carrier with 6 U of uricase. The third reagent zone contains two reagent carriers each with 6 U uricase, 3 mg. tris/citrate buffer (pH 7) and 20 U peroxidase (POD). The reagent strip, which is stable for a year when stored in a dry atmosphere at ambient temperature, is eluted in the manner described in Example 2. A reagent solution is obtained with the following composition:

potassium phosphate buffer (pH 7.0): 0.1 mole/l.
EHT: 1 mMole/l.
detergent: 0.5%
SMBTH: 0.2 mMole/l.
potassium ferrocyanide: 20 mg./l.
uricase: 255 U/l.
POD: 470 U/l.

The uric acid content in serum is determined by adding 0.050 ml. of sample to 2 ml. of this reaction solution and, after incubating for 20 minutes at 20° to 25° C., determining the extinction at Hg 578 nm against a standard.

In an analogous manner, known test combinations for glucose (GOD/PAP method), cholesterol (CHOD/PAP method) and glutamate-pyruvate transaminase (UV method) are applied to reagent strips. The stability and functioning thereof corresponds to the preceding Examples.

It will be understood that the specification and examples are illustrative but not limitative of the present invention and that other embodiments within the spirit and scope of the invention will suggest themselves to those skilled in the art.

What is claimed is:

1. A method of reagent elution from a reagent strip having an elongated handle and a dry, absorbent carrier impregnated with a reagent on one end of the handle, the method comprising: providing a thin mesh stuck onto the handle at opposite sides of the absorbent carrier, substantially covering the absorbent carrier, and pressing the absorbent carrier toward the handle and another mesh between the handle and the absorbent carrier for improving the quantitative elution and the rate of elution of the reagent into a liquid when the absorbent carrier is immersed therein; and immersing the absorbent carrier in the liquid for the elution.

2. The method of claim 1, and further comprising: making the handle and the mesh of synthetic resin and the absorbent carrier of fleece or paper of at least one material selected from the group consisting of cotton, cellulose, regenerated cellulose, polyamide, and polyester.

3. The method of claim 1, wherein the liquid comprises only an appropriate solvent or diluent.

4. The method of claim 1 for the analysis of a test material, comprising:
after immersing the absorbent carrier in the liquid into which the reagent therein elutes, combining at least part of each of the liquid and test material; and detecting any physio-chemical change in the combined liquid and test material thereby effected for the analysis of the test material.

5. The method of claim 1 wherein the liquid is a test liquid, and further comprising:
detecting any physio-chemical change in the test liquid thereby effected for the analysis of the test liquid.

6. The method of claim 1, wherein providing the other mesh comprises providing the same with a mesh size in the range of from about 80$\mu$ to about 250$\mu$ and a mesh filament thickness of from about 10$\mu$ to about 50$\mu$.

7. The method of claim 6, wherein providing the other mesh comprises providing the same with a mesh size in the range of from about 100$\mu$ to about 200$\mu$.

8. The method of claim 1, and additionally comprising: providing at least one more such absorbent carrier and meshes on the handle spaced side-by-side with the first-mentioned one.

9. The method of claim 1, and additionally comprising:
providing at least one more absorbent carrier under the thin mesh in sandwich-like fashion with the first-mentioned absorbent carrier, one overlying the other.

10. The method of claim 8 or 9, and further comprising:
providing the absorbent carriers respectively with different reagents.

11. The method of claim 9, and additionally comprising:
providing an intermediate mesh between the overlying absorbent carriers.

12. The method of claim 11, and further comprising:
providing the intermediate mesh with a mesh size in the range of from 80$\mu$ to about 250$\mu$ and a mesh filament thickness of from 10$\mu$ to about 50$\mu$.

13. The method of claim 12, and further comprising:
providing the other mesh with a mesh size in the range of from about 100$\mu$ to about 200$\mu$.

14. In a reagent strip having an elongated handle and a dry, absorbent carrier impregnated with a reagent on one end of the handle, the improvement comprising:
means comprising a thin mesh stuck onto the handle at opposite sides of the absorbent carrier, substantially covering the absorbent carrier, and pressing the absorbent carrier toward the handle; and means comprising another mesh between the handle and the absorbent carrier for improving the quantitative elution and the rate of the elution into the liquid when the absorbent carrier is immersed therein.

* * * * *